United States Patent
Guetta et al.

(10) Patent No.: US 7,586,596 B2
(45) Date of Patent: Sep. 8, 2009

(54) FIELD FOLDING OPTICAL METHOD FOR IMAGING SYSTEM

(75) Inventors: Avishay Guetta, Rehovot (IL); Doron Korngut, Modiin (IL); Gil Blai, Ramt-Gan (IL); Yoni Cohen, Jerusalem (IL)

(73) Assignee: Applied Materials, Israel, Ltd., Rehovot (IL)

( * ) Notice: Subject to any disclaimer, the term of this patent is extended or adjusted under 35 U.S.C. 154(b) by 366 days.

(21) Appl. No.: 11/426,054

(22) Filed: Jun. 23, 2006

(65) Prior Publication Data

US 2007/0008520 A1 Jan. 11, 2007

Related U.S. Application Data (60) Provisional application No. 60/693,686, filed on Jun. 24, 2005.

(51) Int. Cl.
G01N 21/00 (2006.01)
(52) U.S. Cl. .............. 356/237.2; 356/237.1; 356/237.5; 356/328; 382/145; 382/286
(58) Field of Classification Search ... 356/237.1–237.6, 356/239.3, 239.7, 239.2, 73.1, 328; 382/145, 382/286

See application file for complete search history.

(56) References Cited

U.S. PATENT DOCUMENTS

| | | | | |
|---|---|---|---|---|
| 5,448,364 | A | * | 9/1995 | Moran ..................... 356/237.3 |
| 6,597,006 | B1 | * | 7/2003 | McCord et al. .......... 356/237.2 |
| 7,106,425 | B1 | * | 9/2006 | Bultman et al. ............... 356/73 |
| 7,248,354 | B2 | * | 7/2007 | Kreh et al. ............... 356/237.5 |

* cited by examiner

Primary Examiner—Gregory J Toatley, Jr.
Assistant Examiner—Iyabo S Alli
(74) Attorney, Agent, or Firm—Tarek N. Fahmi (57) ABSTRACT

Apparatus for inspecting a surface of a sample, including a detector and folding optics. The folding optics are configured to receive radiation arising from a first region of the surface and from a second region of the surface. The first region and the second region have a first spatial relationship with respect to each other. The folding optics form from the radiation a first image of the first region and a second image of the second region on the detector, wherein the first image is a linear transformation of the first region and the second image is the linear transformation of the second region. The first image and the second image have a second spatial relationship, different from the linear transformation of the first spatial relationship, with respect to each other.

23 Claims, 8 Drawing Sheets

FIELD FOLDING OPTICAL METHOD FOR IMAGING SYSTEM

CROSS-REFERENCE TO RELATED APPLICATION

This application claims the benefit of U.S. Provisional Patent Application No. 60/693,686, filed 24 Jun. 2005, which is incorporated herein by reference.

FIELD OF THE INVENTION

The present invention relates generally to inspection of a surface, and specifically to scanning methods for inspecting the surface of a wafer in a fabrication facility.

BACKGROUND OF THE INVENTION

In a wafer fabrication facility, optical scanning is one of the recognized methods for inspecting the wafer. The scanning irradiates a specific region of the wafer, for instance in a die or cell on the wafer, and measures one or more parameters of the returning radiation. The measured parameters may be compared with other respective "standard" parameters, typically in a cell-cell or die-die comparison, or in a comparison against previously determined values, to determine if the irradiated region is within specification.

Typically, the complete wafer is scanned in a series of equal-width slices, the wafer being translated by its mounting stage while the one or more beams inspecting the wafer scan orthogonally to the direction of the translation.

SUMMARY OF THE INVENTION

In an embodiment of the present invention, a surface, for example the surface of a wafer in a wafer fabrication facility, is irradiated with one or more radiation beams produced in a surface inspection apparatus. The beams irradiate first and second regions on the surface, typically by scanning within the regions. To inspect the surface, the regions are translated with respect to the surface, so that an area of the surface to be inspected is traversed by one or other of the regions. The surface inspection apparatus sets the two regions to have a surface spatial relationship with respect to each other. Typically, the surface spatial relationship is set so that translations of the regions over the surface may be performed without the paths of the two regions overlapping. Alternatively, at least a portion of the paths may overlap.

In some embodiments the regions are congruent rectangles having the same orientation. In one embodiment the surface spatial relationship sets the shorter sides of the rectangles to touch. In an alternative embodiment, the rectangles do not touch.

The apparatus comprises folding optics which receive radiation arising from the two regions, and which form respective images of the regions on a radiation detector, for example a charge coupled device (CCD) array or an image intensifier array. A linear transformation relates the images of the regions to the regions themselves, so that the images are undistorted images of the regions. The folding optics cause the two images on the detector to have a detector spatial relationship which is different from the spatial relationship generated by applying the linear transformation to the surface spatial relationship. The change in spatial relationship enables the inspection apparatus to be configured more flexibly and to operate more efficiently, since the folding optics ensure independence between the surface spatial relationship and the detector spatial relationship. The independence between the relationships allows the detector to be "filled" more completely for a given surface spatial relationship, enabling the surface to be scanned faster with no reduction in signal to noise ratio.

The folding optics may be constructed in a number of different forms. In one embodiment, the optics comprise two sets of fiber optic bundles which are bent to implement the difference in spatial relationship. In another embodiment, the optics comprise a grating, different orders of the diffracted images being used to generate the spatial relationship difference. In other embodiments, the folding optics comprise one or two sets of reflecting surfaces arranged as periscopes. In yet another embodiment, the optics comprise a beamsplitter.

The present invention will be more fully understood from the following detailed description of the embodiments thereof, taken together with the drawings in which:

DETAILED DESCRIPTION OF EMBODIMENTS

Figure 1:
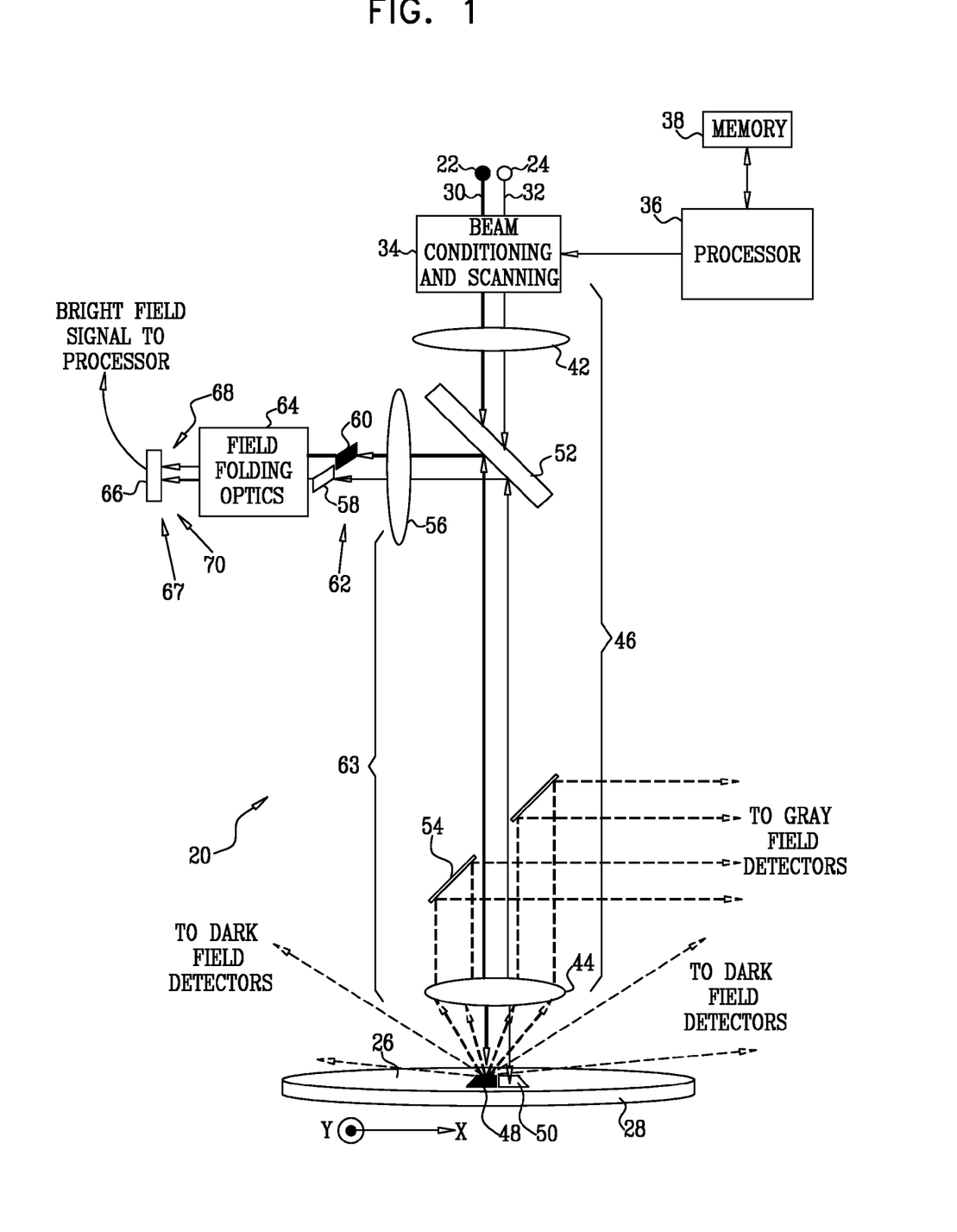
FIG. 1 is a schematic diagram of an inspection apparatus, according to an embodiment of the present invention.

FIG. 1 is a schematic diagram of an inspection apparatus 20, according to an embodiment of the present invention. Apparatus 20 comprises two sources 22, 24, of radiation, the two sources typically having substantially the same wavelength, the sources forming respective beams 30, 32, that are used to irradiate a surface 26. Herein, by way of example, surface 26 is assumed to comprise the surface of a wafer 28, but it will be appreciated that embodiments of the present invention may be used for irradiation and/or inspection of substantially any surface. Surface 26 is assumed to define an x-y plane, with the x-axis lying in the plane of the paper, and the y-axis coming out of the paper, as shown in FIG. 1.

Sources 22, 24 are typically lasers, although any other suitable source or sources of radiation may be used to generate beams 30, 32.

Beams 30, 32 enter a beam conditioning and scanning module 34. Module 34 conditions the beams by focusing and/or expanding and/or multiplexing them. Module 34 also scans the beams, typically using rotating mirrors and/or acousto-optic deflectors. Elements for performing all the functions of module 34 are well known in the art. Module 34 is controlled by a processor 36, which also operates other elements of apparatus 20. Processor 36 is coupled to a memory 38, wherein are stored instructions for operation of the apparatus.

Module 34 is part of a set of projection optics elements 46, which also include other elements, indicated schematically in FIG. 1 by a relay lens 42 and an objective lens 44. Projection optics 46 function to project radiation onto two regions 48, 50 of surface 26. Optics 46 also include a beamsplitter 52, which allows transmission of beams 30, 32 to surface 26. Regions 48, 50 are assumed, by way of example, to be rectangles having the same orientation. The regions are separated by a surface spatial relationship which is determined by projection optics 46, and which may be described by a vector. Regions 48, 50 and the spatial relationship between them are described in more detail below.

Returning radiation from regions 48, 50 is typically of three forms: bright field radiation, comprising radiation which is substantially specularly reflected from surface 26, dark field radiation, which is typically radiation which is scattered from surface 26 at relatively large angles, of the order of 30° or more, to the path of the specular reflected radiation, and gray field radiation, which is scattered from surface 26 at angles between the path of the specular reflected radiation and the dark field radiation.

Generally, in inspecting surface 26, all three forms of returning radiation are measured. The measurement is made by respective detectors for each of the radiations, the gray field radiation and the dark field radiation each typically using a plurality of detectors. Embodiments of the present invention may be advantageously used for all types of returning radiation from surface 26. For the purposes of clarity, however, the description herein is directed only to specular returning radiation. Those having ordinary skill in the art will be able to adapt the description, mutatis mutandis for gray field and dark field radiation.

In apparatus 20 beams 30 and 32 are arranged to be incident substantially normally on surface 26, although the apparatus could be set to operate at non-normal angles of incidence. A mirror 54 has a hole at its center to allow free passage of beams 30 and 32, as well as returning specular radiation from regions 48, 50. Mirror 52 reflects gray field radiation from the regions to gray field detectors, which are not shown in FIG. 1. Dark field detectors, also not shown in FIG. 1, receive dark field radiation from regions 48, 50.

Specular radiation from regions 48, 50 traverses objective 44, and is reflected by beamsplitter 52 to a lens 56. Lens 56 focuses the radiation to form respective images 58, 60 of regions 48, 50 at a plane 62. Objective 44, beamsplitter 52, and lens 56 are part of a set of receiving optics 63 which have as conjugate focal planes plane 62 and surface 26. Receiving optics 63 act to apply a linear transformation to regions 48, 50 so that the images of the regions are substantially undistorted. The receiving optics also apply the same linear transformation to the surface spatial relationship, so that in addition to the images of the regions themselves being substantially undistorted, the spatial relationship between the images is substantially undistorted. In the specification and in the claims, a linear transformation is assumed to comprise one or more translations, rotations, reflections and/or dilatations.

Radiation from images 58 and 60 enters a field folding optics module 64, and from there is focused onto a bright field receiver 66, forming respective receiver images 68, 70 thereon. Receiver 66 comprises a detector 67 which is herein assumed by way of example to comprise an array of detector elements, the array typically being rectangular and having a predetermined aspect ratio. Detector array 67 is typically a charge coupled device (CCD) array or an array of semiconductor elements. In some embodiments receiver 66 comprises an image intensifier (IIT) which precedes array 67. The IIT receives radiation from regions 48, 50, and provides image intensified radiation, i.e., radiation arising from the radiation from the regions, to array 67. Signals from array 67 are transferred to processor 36 for processing and the processed signals are used in the inspection of surface 26.

The function of module 64 is to change the spatial relationship between images 58 and 60. This typically allows receiver 66 to operate more efficiently. To achieve this increase in efficiency, module 64 changes the spatial relationship of images 58 and 60 so that an overall aspect ratio of images 68, 70 corresponds more closely with an aspect ratio of detector array 67.

Figure 9:
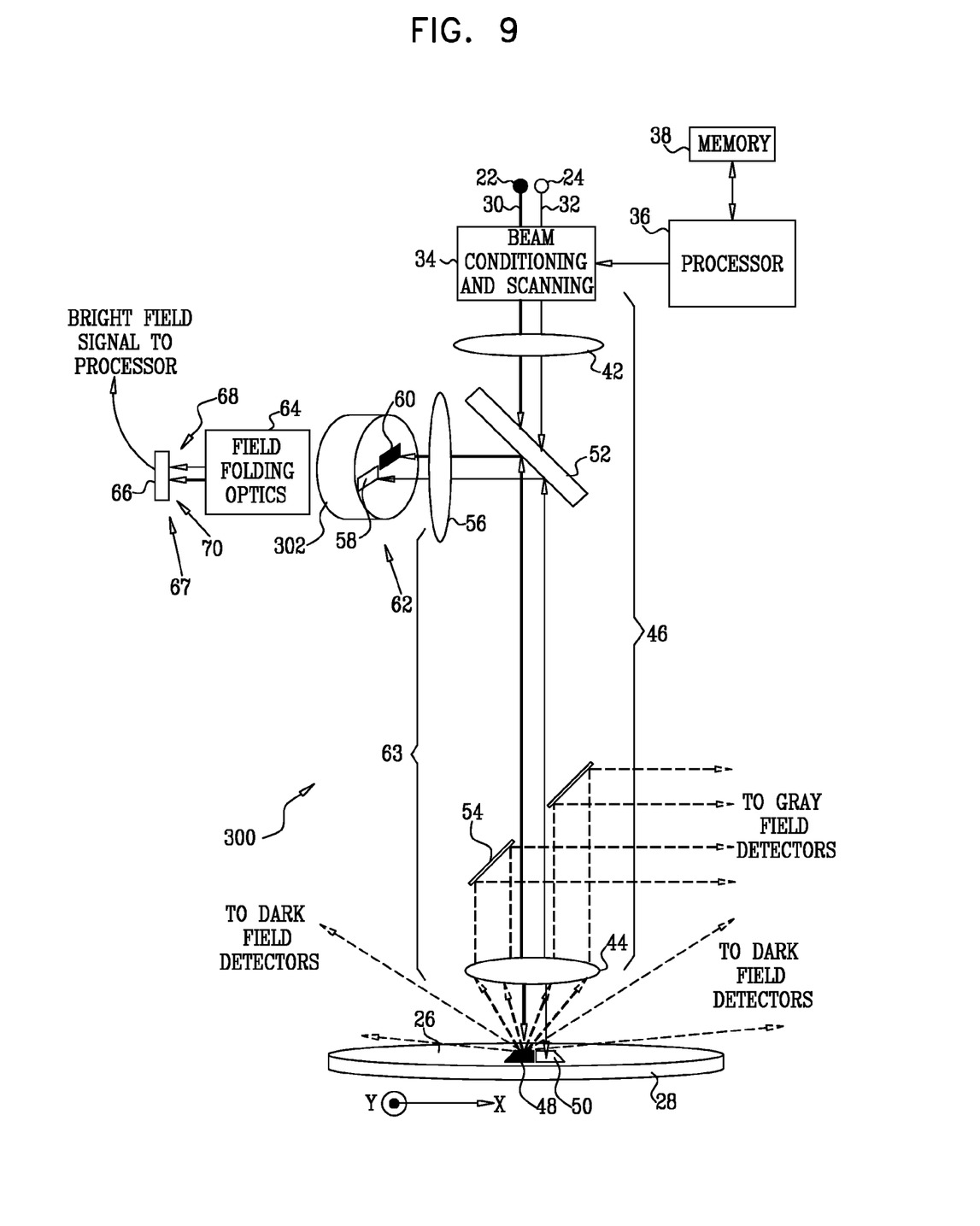
FIG. 9 is a schematic diagram of an inspection apparatus, according to an alternative embodiment of the present invention.

In an embodiment of the present invention described in more detail with respect to FIG. 9, an IIT precedes module 64.

As will be apparent from the description below, module 64 performs the change of spatial relationship between images 58, 60, substantially without distortion of the images themselves, to generate images 68, 70. Thus, module 64 applies an overall linear transformation to each of regions 48, 50, to form respective images 68, 70. However, module 64 does not apply the overall linear transformation to the surface spatial relationship between regions 48, 50. Rather, the spatial relationship between images 68, 70 is a function of the construction of module 64, and is substantially independent of the surface spatial relationship between regions 48, 50.

Figure 2:
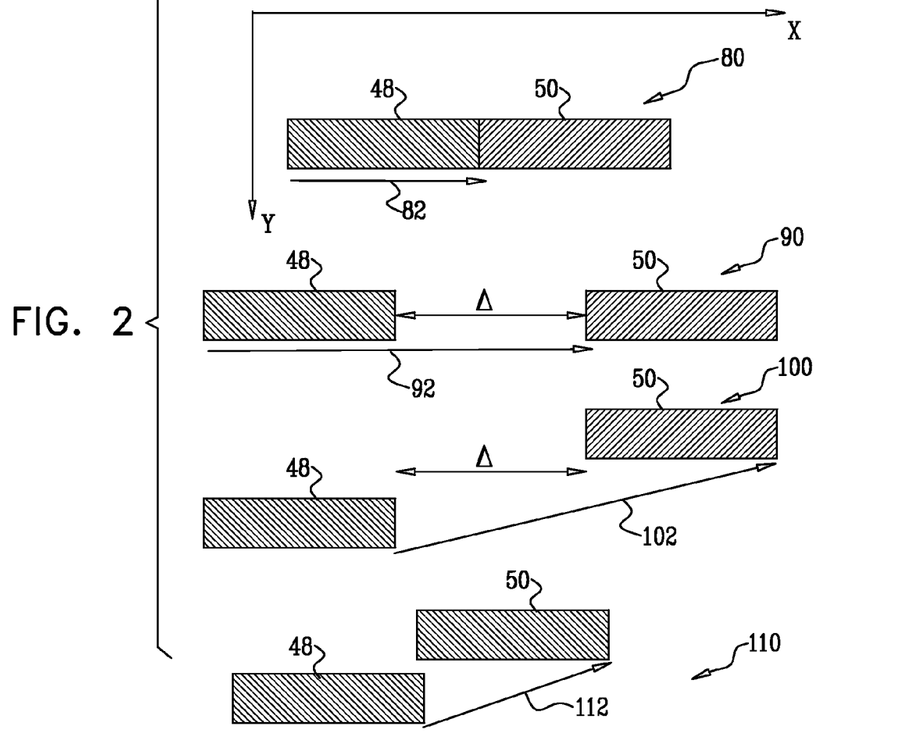
FIG. 2 is a schematic diagram showing examples of different possible surface spatial relationships between regions on a surface, according to an embodiment of the present invention.
Figure 3:
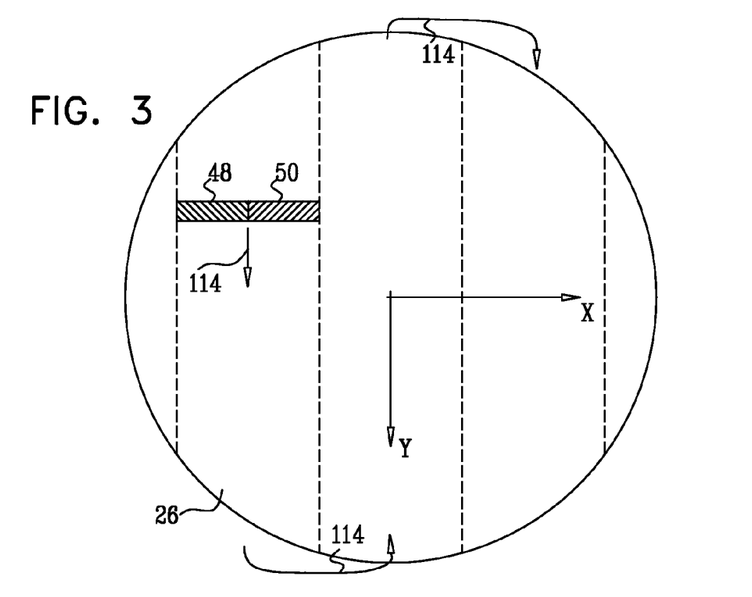
FIG. 3 is a schematic diagram showing translation of the regions of FIG. 2 relative to the surface, according to an embodiment of the present invention.

FIG. 2 is a schematic diagram showing examples of different possible surface spatial relationships between regions 48 and 50, and FIG. 3 is a schematic diagram showing translations of the regions relative to surface 26 of wafer 28, according to embodiments of the present invention. Regions 48, 50 are assumed to be congruent rectangles having the same orientation, with their long sides parallel to the x-axis of surface 26 (FIG. 1). The rectangles have a width W and a height H. Regions 48, 50 are generated by projection optics 46, and each region corresponds to a rectangle which bounds locations on surface 26 irradiated by a conditioned beam. Each region is typically formed by a spot generated by the conditioned beam being scanned, for example in a raster pattern, over the region. In some embodiments the beam conditioning comprises forming a multiplicity of spots on surface 26, and the multiplicity of spots are scanned over the region.

In order to inspect surface 26, regions 48 and 50 are swept over surface 26 so that substantially all the surface is irradiated with one or other of beams 30, 32. In some embodiments, at least part of surface 26 may be irradiated by both beams. Typically the sweeping is performed by translating wafer 28 on an x-y stage, using a set of translations 114 such as that illustrated in FIG. 3. In order to inspect surface 26 in as short a time as possible, the number of sweeps in the y-direction should be as few as possible, so that the width of the swept area should be as wide as possible. Embodiments of the present invention accomplish this by setting the widths W accordingly. However, while in the examples of spatial relationships for regions 48 and 50 described herein, the widths and/or heights of the regions are assumed equal, this is not a necessary condition for embodiments of the present invention, and those having ordinary skill in the art will be able to adapt the description herein for regions having unequal widths and/or heights.

In a first example 80, regions 48 and 50 are set to touch so that a vector 82 giving the spatial relationship between the regions is an ordered pair (W, 0). The sweeping of the regions necessary to scan surface 26 is illustrated in FIG. 3

In a second example 90, regions 48 and 50 are separated by a horizontal distance Δ, which is set to equal W. A vector 92 (2W, 0) describes the spatial relationship between the two regions.

In a third example 100, regions 48 and 50 are separated by a spatial relationship given by a vector 102 (2W, h) where h is a non-negative number.

In a fourth example 110, regions 48 and 50 are separated by a spatial relationship given by a vector 112 (w, h) where w<W and h is a non-negative number.

Translations 114 illustrated in FIG. 3 are modified as necessary to accommodate the separation between the regions given in examples 90, 100, and 110.

Other surface spatial relationships between regions 48 and 50 will be apparent to those having ordinary skill in the art. The translations necessary to accommodate the spatial relationships illustrated in examples 90, 100, and 110, as well as the other spatial relationships, may be arranged so that no region of surface 26 is irradiated by both beams 30, 32. Alternatively, the translations may be arranged so that at least some areas of surface 26 are irradiated by both beams.

In the case of scanning a complete wafer, it will be appreciated that for a given rate of translation by the mounting stage and assuming a given time for scanning a region, the time taken to scan the complete wafer depends on the width of the slices, since wider slices lead to fewer slices having to be scanned. Thus, in order to reduce the wafer scanning time to a minimum, slices illustrated in FIG. 3 are typically configured to be as wide as possible.

Embodiments of the present invention allow the aspect ratio of the scanned regions and detector arrays to be independent of each other, so that detector arrays having a standard aspect ratio may be efficiently used with scan regions of a different aspect ratio.

Figure 4:
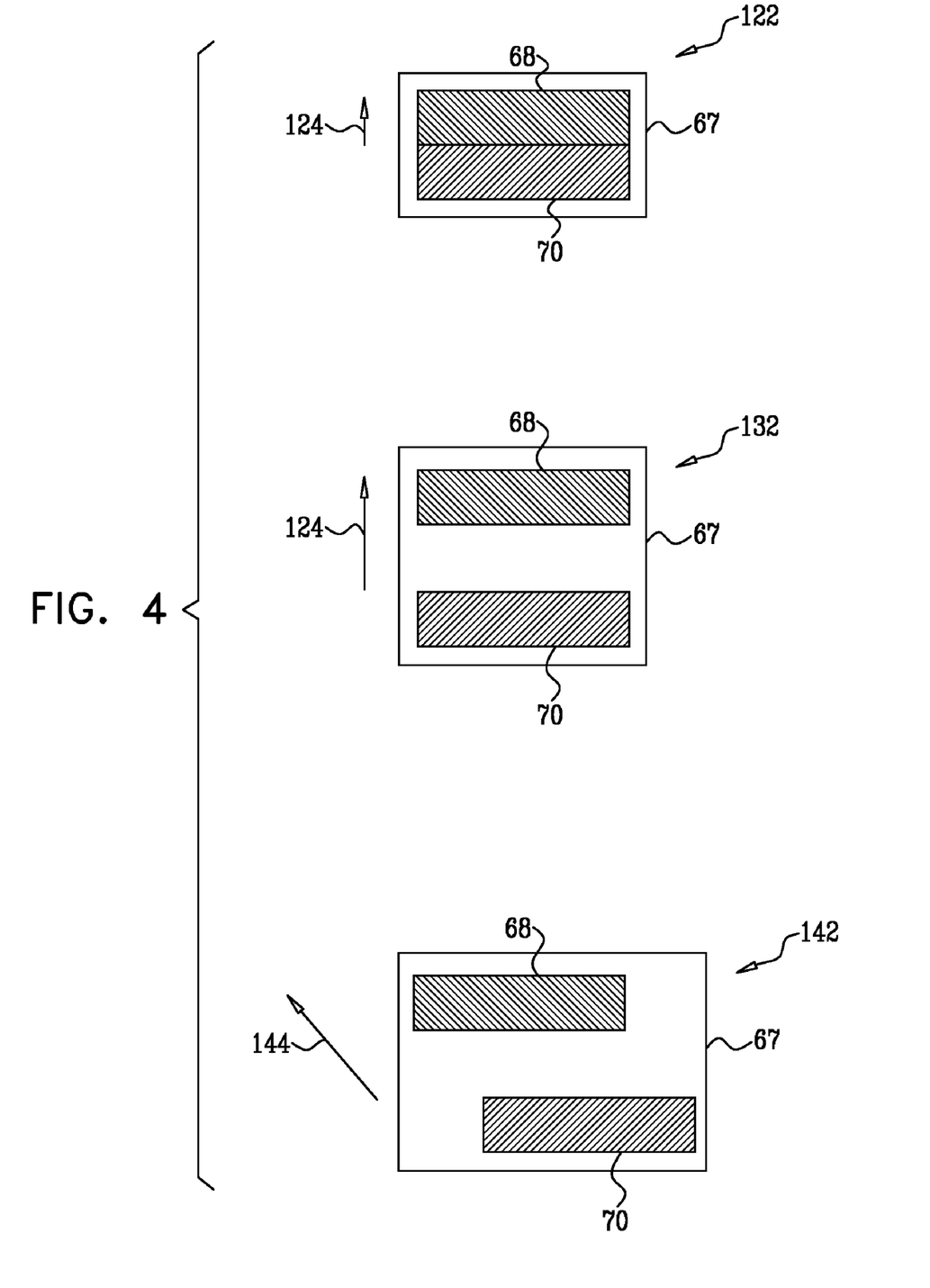
FIG. 4 is a schematic diagram of examples illustrating how receiver images may be arranged on a detector array, according to an embodiment of the present invention.

FIG. 4 is a schematic diagram of examples illustrating how receiver images 68, 70 may be arranged on array 67, according to an embodiment of the present invention. Images 68 and 70 are in the form of congruent rectangles having a width W' and a height H'. Dimensions of images 48, 50 and 68, 70 are related by equation (1):

$$\frac{W}{H} = \frac{W'}{H'} \tag{1}$$

In an example 122, a spatial relationship between image 68 and image 70 may be represented by a vector 124 (0, H'), so that the images touch at their long sides, and there is no horizontal displacement between the images.

In an example 132, a vector 134 (0, J), where J>H', represents the spatial relationship between the two images. As for example 122, there is no horizontal displacement between the images. In contrast with example 122, the two images do not touch.

In an example 142, a vector 144 (K, J), where K is a non-zero value and J>H', represents the spatial relationship between the two images. The images do not touch, and there is a horizontal displacement between them.

Comparison of the spatial relationships for images 68, 70 with those of images 48, 50, shows that the relationships are different. The spatial relationships for images 68, 70 allow array 67 to be "filled" more completely, compared to systems where the spatial relationship is unchanged. The more complete filling of the array increases the efficiency of operation of apparatus 20.

Figure 5:
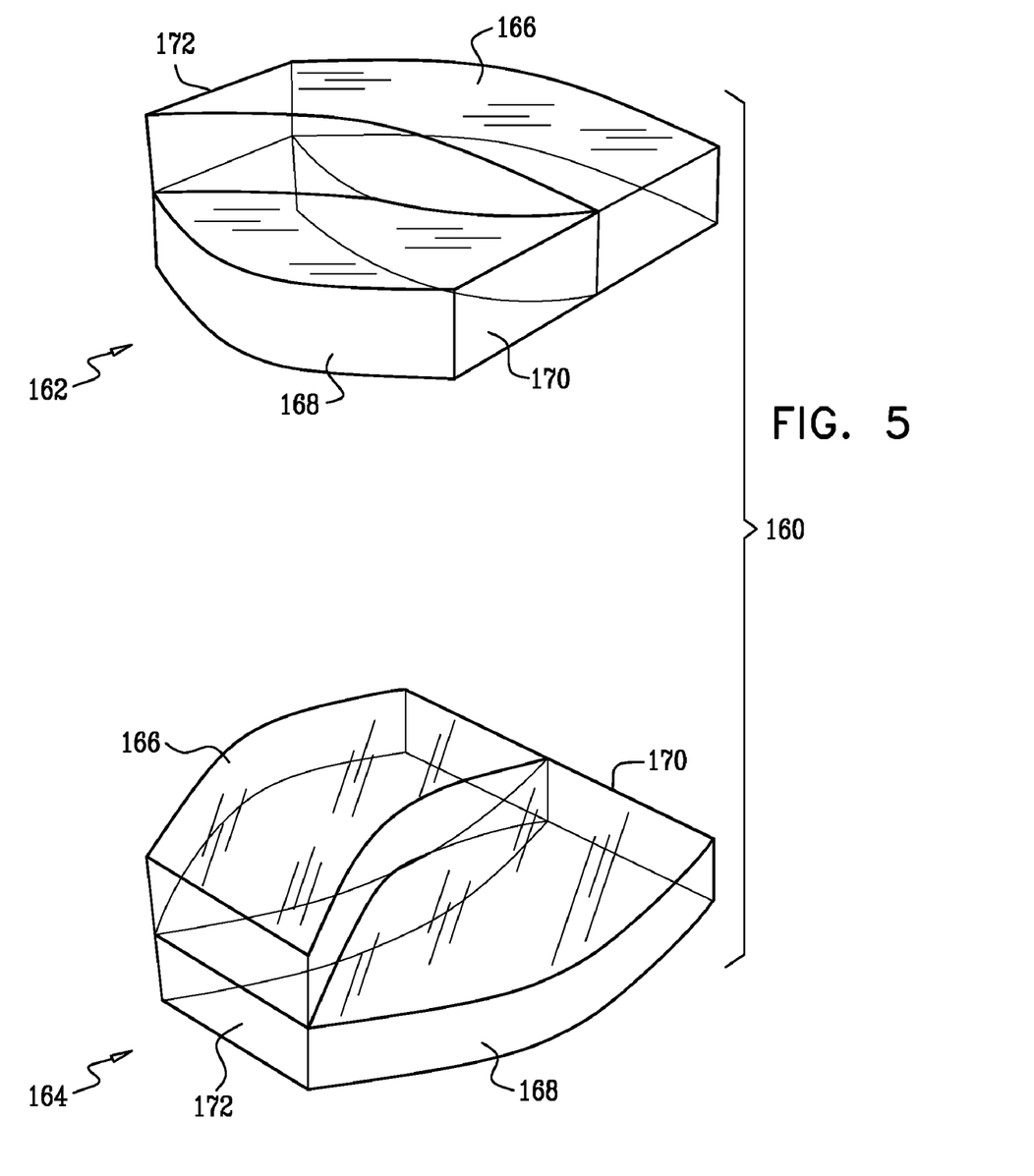
FIG. 5 is a schematic diagram of a component in a field folding optics module, according to an embodiment of the present invention.

FIG. 5 is a schematic diagram of a component 160 in folding module 64, according to an embodiment of the present invention. Two views, a first view 162 and a second view 164, are shown of component 160. Component 160 comprises a set 166 and a set 168 of fiber optic bundles, each of the sets being folded. A first side 170 of component 160 receives images 58 and 60, and the radiation from the images is conveyed over the respective sets of fiber optic bundles to a second side 172 of the component. The radiation from second side 172 is focused onto array 67 as images 68, 70. It will be appreciated that module 64 may typically include other optical elements, such as lenses, to perform the conversion of images 58, 60 to images 68, 70. Alternatively, component 160 may perform at least some of the conversion functions itself, for example, by side 172 butting onto array 67.

Component 160 may be used to convert images of regions 48, 50 shown in example 80 (FIG. 2) to those of images 68, 70 shown in example 122 (FIG. 4). However, it will be understood that embodiments of the present invention comprise other configurations of set 166 and set 168, such as configurations that would convert images of examples 90, 100, or 110 (FIG. 2) to one of images of examples 122, 132, or 142 (FIG. 4). All such configurations are comprised within the scope of the present invention.

Since virtually all the radiation entering side 170 exits from side 172, it will be understood that the spatial relationship conversion performed by component 160 entails substantially no loss of energy.

Figure 6:
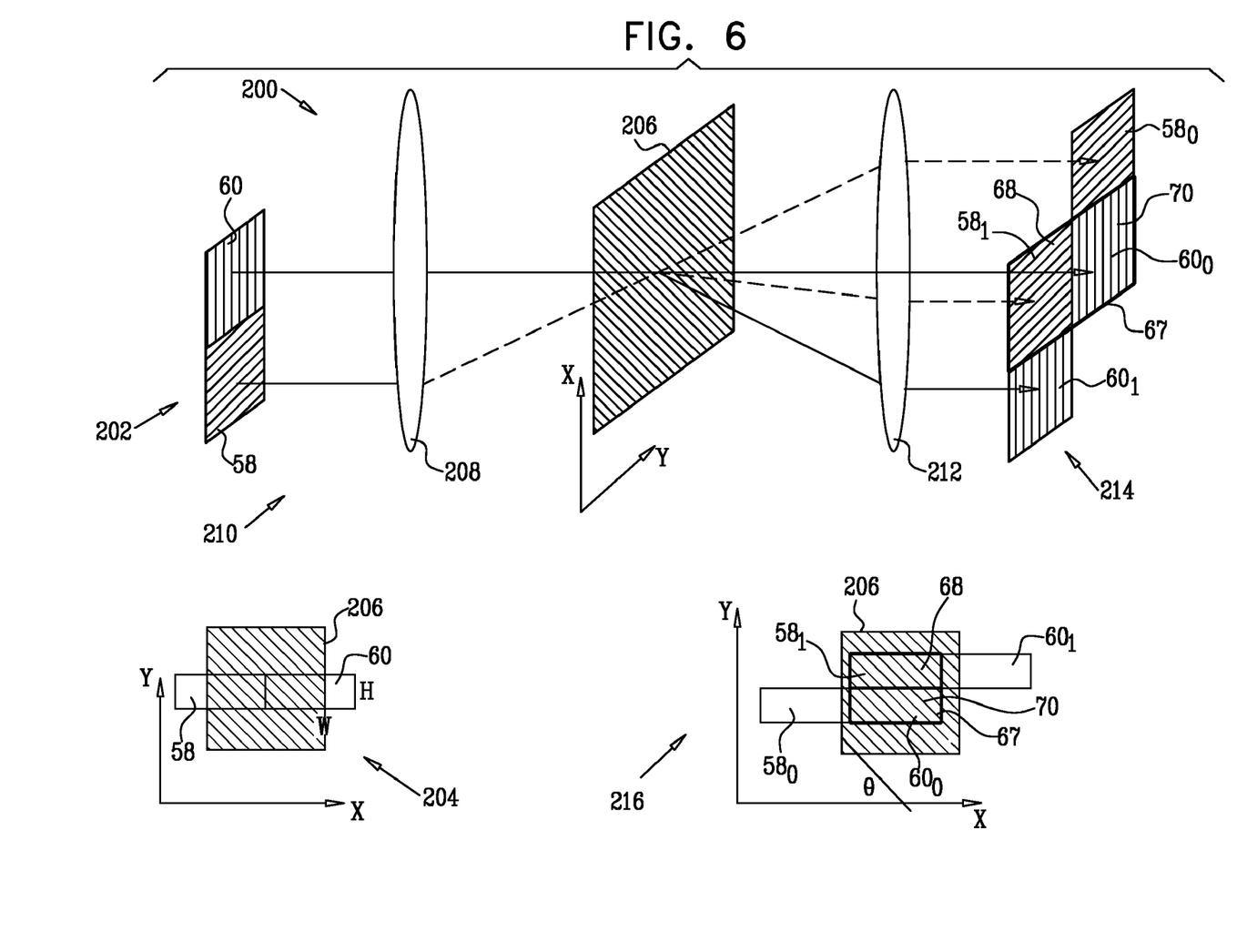
FIG. 6 shows schematic diagrams of a component in the folding module, according to an alternative embodiment of the present invention.

FIG. 6 shows schematic diagrams of a component 200 in folding module 64, according to an alternative embodiment of the present invention. The following description of component 200 is drawn to performing substantially the same type of conversion of spatial relationships as is performed by component 160 (FIG. 5), and changes to the description will be apparent to those skilled in the art so as to accommodate the other spatial relationship conversions comprised in embodiments of the present invention. A diagram 202 is a schematic perspective view of component 200. Component 200 comprises a collimating objective lens 208, which is positioned so that its focal plane 210 is at the position of plane 62 (FIG. 1). Collimated light from images 58, 60 passes through a diffraction grating 206 and then through a decollimating lens 212. For clarity, the description of component 200 assumes that grating 206 defines a local set of x-y axes in the plane of the grating. Lens 212, typically a tube lens, focuses the diffracted collimated light from grating 206 to an image plane 214, corresponding with the surface of array 67.

A diagram 204 shows images 58, 60, and grating 206, as viewed in a direction perpendicular to the x-y axis. The shading of grating 206 gives an approximate direction of the lines of the grating. A diagram 216 shows grating 206 and images generated by the grating, viewed in a direction perpendicular to the x-y axis. Grating 206 diffracts the radiation from images 58, 60 into zero and first orders, labeled in diagrams 202 and 216 with subscripts: $58_0$, $58_1$, $60_0$, and $60_1$ respectively. The zero order radiation passes substantially undeflected through the grating, and first order radiation is deflected at right angles to the lines of the grating. Grating 206 and lenses 208 and 212 are arranged so that first order image $58_1$ corresponds to image 68, and so that the zero order image $60_0$ corresponds to image 70. The position of array 67 is also shown in diagrams 202 and 216. The spatial relationships difference between the two sets of images (images 58, 60, and images 68, 70) correspond to those given for component 160, and in this case the lines of grating 206 are at an angle θ to the x-axis given by equation (2):

$$\theta = \arctan\frac{H}{W} \tag{2}$$

Although grating 206 may diffract received radiation into orders other than the zero and first orders shown in FIG. 6, methods are well known in the optical arts for concentrating the diffracted radiation into specific orders, and these methods may be advantageously applied to grating 206 in production of the zero and first orders required for component 200. If necessary, stops may be introduced into component 200 in order to prevent unwanted radiation reaching array 67.

It will be understood that by changing angle θ, and/or by using diffraction order pairs other than the zero and first order pair exemplified above, and/or by varying the parameters of grating 206 and/or lenses 208 and 212, embodiments similar to component 200 may be configured to generate substantially any spatial relationship conversion required.

Those having ordinary skill in the art will appreciate that the spatial relationship conversion performed by grating 206 may also be performed by a partially reflecting beamsplitter instead of the grating. If a beamsplitter is used, one of images 68, 70 is a transmitted image, the other of images 68, 70 is a reflected image.

Figure 7A:
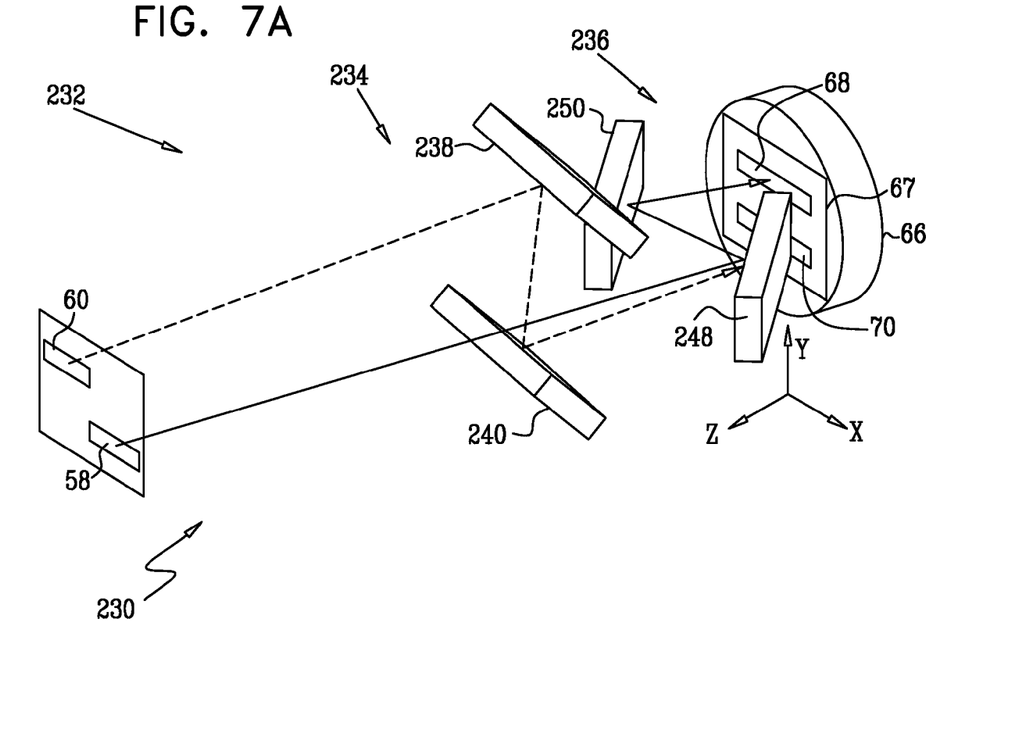
FIGS. 7A and 7B show schematic diagrams of a component in the folding module, according to a further alternative embodiment of the present invention.
Figure 7B:
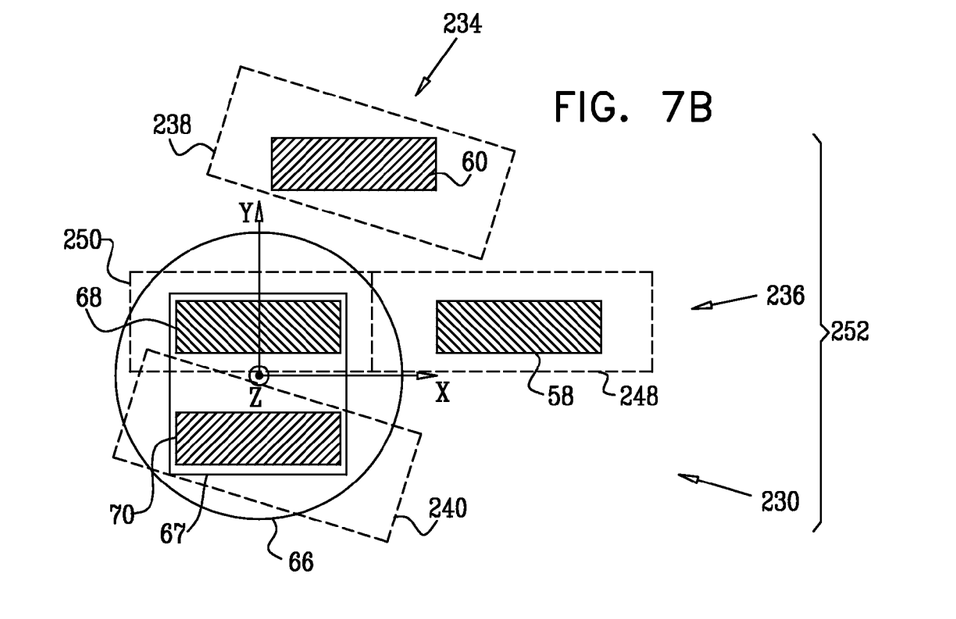

FIGS. 7A and 7B show schematic diagrams of a component 230 in folding module 64, according to a further alternative embodiment of the present invention. The following description of component 230 is drawn to images 58, 60 having a spatial relationship similar to example 110 (FIG. 2), the images being converted to images 68, 70 having a spatial relationship similar to example 132 (FIG. 4). A diagram 232 is a schematic perspective view of component 230. A diagram 252 is a view towards receiver 66, showing relations between different elements of the embodiment in a cross-sectional form. For clarity in the description of the embodiment, a local set of x, y, z axes are assumed to be defined with reference to array 67, as shown in the diagrams. The local set of axes has its origin in array 67, with the local z-axis normal to the array, and the directions of the local x and y axes defined by the directions of the array elements. (Also for clarity, in FIG. 7A the local set of axes is shown displaced from array 67.) It will be understood that the local set of axes is not necessarily related to the axes described above with reference to wafer 26, or to the local set of axes used for the description of component 200.

Component 230 comprises two sets of periscopes 234, 236. Each periscope is formed of two parallel plane mirrors, so that periscope 234 comprises mirrors 238 and 240, and periscope 236 comprises mirrors 248 and 250. For clarity, optical elements in component 230 other than the mirrors are not shown in FIGS. 7A and 7B. Such optical elements, such as one or more relay lenses, will be apparent to those having ordinary skill in the art.

Each mirror of periscopes 234, 236 is a rectangle having a respective center of symmetry. The two mirrors of one periscope each have a normal through the respective centers of symmetry of the mirrors, and the two normals define a plane, herein termed the "periscope plane." Each periscope acts to translate the radiation it receives, and thus the image formed by the periscope, in its periscope plane.

Periscope 234 is positioned so that it does not obstruct the radiation transferred by periscope 236. Similarly, periscope 236 is positioned so that the radiation transferred by periscope 234 is not obstructed. The non-obstruction is typically accomplished by "tilting" the periscope planes with respect to each other, as described hereinbelow. The tilting causes the periscope planes to be non-perpendicular.

In embodiments similar to component 230, the periscope plane of periscope 236 is parallel to the x-z plane, having an equation given by equation (3):

$$\{(x,y,z)|y=k,x,y,z\in R\} \tag{3}$$

The periscope plane of periscope 234 is parallel to the z-axis. The equation of the periscope plane of periscope 234 is given by equation (4):

$$\{(x,y,z)|y=mx+c,m,c,x,y,z\in R\} \tag{4}$$

In equations (3) and (4), values of k, m and c are chosen so that, as described above, there is no obstruction of radiation by either periscope. For example, k>0, m>0, and c≈0 in component 230.

In some embodiments of the present invention, one or more of plane mirrors 238, 240, 248, 250 are replaced by a curved reflecting elements, the curvature of the reflecting elements being used to perform functions that are typically performed by other optical elements comprised in apparatus 20. In this case, the other optical elements may be removed from the apparatus.

Figure 8:
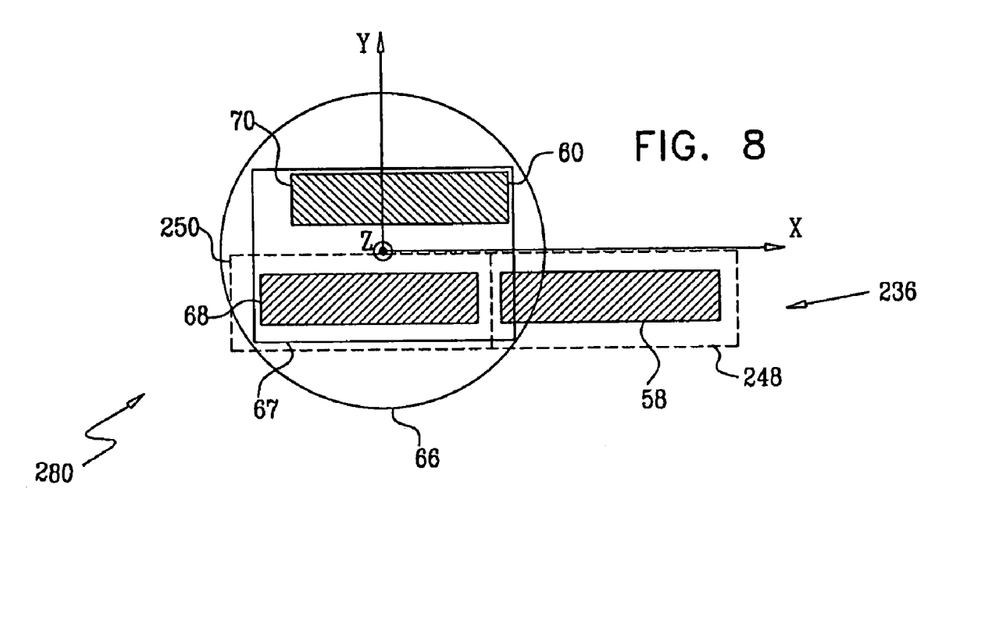
FIG. 8 shows a schematic cross-sectional view of a component in the folding module, according to a yet further alternative embodiment of the present invention.

FIG. 8 shows a schematic cross-sectional view of a component 280 in folding module 64, according to a yet further alternative embodiment of the present invention. Apart from the differences described below, the operation of component 280 is generally similar to that of component 230 (FIGS. 7A and 7B), such that elements indicated by the same reference numerals in both embodiments are generally identical in construction and in operation. The following description of component 280 is drawn to images 58, 60 having a spatial relationship similar to example 110 (FIG. 2) that are converted to images 68, 70 having a spatial relationship similar to example 142 (FIG. 4). Component 280 only uses one periscope 236, rather than the two of component 230. The periscope plane of periscope 236 is configured to be parallel to and below the x-z plane, having an equation given by equation (5):

$$\{(x,y,z)|y=k,k<0,x,y,z\in R\} \tag{5}$$

In component 280, image 70 is formed as a substantially direct transfer of image 60 onto detector array 67, in contrast to the translation of image 60 to image 70 generated in component 230.

In some embodiments of the present invention, the periscopes described herein are configured from transparent and/or partially transparent optical elements, the elements typically including one or more reflecting surfaces. The configuration of periscopes from such elements will be apparent to those having ordinary skill in the optical art.

Figure 10:
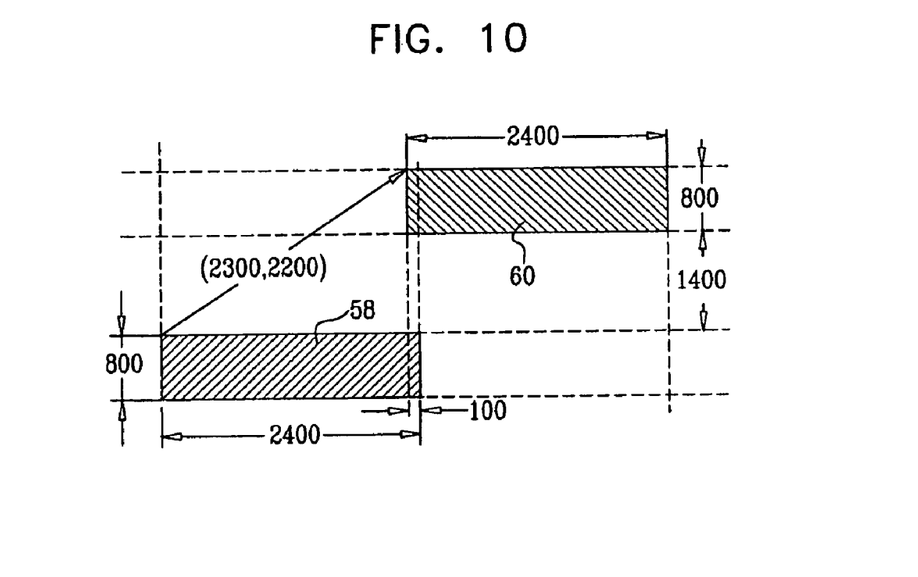
FIG. 10 is a schematic diagram of images formed on an image intensifier comprised in the apparatus of FIG. 9, according to an embodiment of the present invention.

FIG. 9 is a schematic diagram of an inspection apparatus 300 and FIG. 10 is a schematic diagram of images formed on an IIT 302 comprised in apparatus 300, according to an embodiment of the present invention. Apart from the differences described below, the operation of apparatus 300 is generally similar to that of apparatus 20 (FIG. 1), such that elements indicated by the same reference numerals in both apparatus 20 and 300 are generally identical in construction and in operation.

In apparatus 300, IIT 302 precedes module 64, and images 58, 60 are formed on the IIT before they are intensified. FIG. 10 shows dimensions of the images, in pixels, and the separation between the images. The linear transformation applied by receiving optics 63 to regions 48, 50 generates images 58 and 60 each to have dimensions of 2400 by 800 pixels, i.e., with an aspect ratio of 3:1, which is the same aspect ratio as regions 48, 50. The linear transformation of the receiving optics generates a spatial relationship between the images equal to a vector (2300, 2200).

Module 64 alters the spatial relationship between the images, as described above. For example, if the module does not change the size of images 58, 60, but alters the spatial relationship to be similar to example 132 (FIG. 2), then array 67 may be an array of detector elements 2400 pixels by 3000 pixels, and the spatial relationship between images 68, 70 on the array, i.e., vector 124, is (0, 2200).

The embodiments of the present invention described herein generate intermediate images 58, 60 between regions 48, 50 and the final images 68, 70 of the regions. It will be appreciated that the intermediate images may be real or virtual images. It will also be appreciated that embodiments of the present invention may be configured to perform the change of spatial relationship between regions 48, 50 and that of final images 68, 70 without generating intermediate images. For example, in apparatus 20 or 300 the focal length of lenses 44 and/or 56 may be adjusted, and/or at least one of the lenses may be removed or replaced by a curved mirror, so that regions 48, 50 act in place of the intermediate images for module 64. Other embodiments wherein there are no intermediate images will be apparent to those of ordinary skill in the art, and all such embodiments are assumed to be included within the scope of the present invention.

The embodiments described herein have assumed that regions 48, 50 are in the form of rectangles, so that their images are also in the form of rectangles. It will be appreciated, however, that regions 48, 50 may comprise substantially any regular or irregular shape that may be formed on surface 26, and that the images of the regions will have the same shape.

While embodiments of the present invention described hereinabove have assumed two separate beam generators, sources 22 and 24, it will be appreciated that the two separate beams may be generated by one source, for example, by the beam from one source being divided into two beams by a partially reflecting mirror. It will also be appreciated that regions 48, 50 may be irradiated by one beam. The one beam covers both regions, and in some embodiments the one beam may cover more than the regions themselves.

It will also be appreciated that the scope of the present invention includes two or more regions, the two or more regions having a first spatial relationship therebetween, the respective images of the two or more regions being generated by a linear transformation of each of the regions, the images having a second spatial relationship therebetween which is different from the linear transformation of the first spatial relationship.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. Apparatus for inspecting a surface of a sample, comprising:
    a detector; and
    folding optics configured to receive radiation arising from a first region of the surface and radiation arising from a second region of the surface, the first and second regions having a first spatial relationship with respect to each other, the folding optics further configured to form from the radiation a first image of the first region and a second image of the second region on the detector, and the folding optics further configured: (i) such that each of the first and second images on the detector is a linear transformation of the corresponding first and second regions of the surface; (ii) so as to arrange the first and second images on the detector according to a second spatial relationship, different from a linear transformation of the first spatial relationship, with respect to each other; and (iii) so as to arrange, according to the second spatial relationship, the first and second images to more completely fill the detector compared to arranging the first and second images according to the linear transformation of the first spatial relationship.

2. The apparatus according to claim 1, wherein the first and the second regions are non-overlapping regions.

3. The apparatus according to claim 1, further comprising a first source which provides irradiation to the first region, and a second source which provides irradiation to the second region, and wherein the irradiation of the first and second regions causes the radiation received by the folding optics.

4. The apparatus according to claim 1, wherein the first region is congruent with the second region.

5. The apparatus according to claim 4, wherein the first and the second regions have the same orientation.

6. The apparatus according to claim 4, wherein the first and second regions comprise rectangles.

7. The apparatus according to claim 1, wherein the folding optics comprises at least one fiber optic bundle.

8. The apparatus according to claim 7, wherein the at least one fiber optic bundle comprises a first fiber optic bundle which receives the radiation arising from the first region and which is configured to transfer the radiation arising from the first region to the first image and a second fiber optic bundle which receives the radiation arising from the second region and which is configured to transfer the radiation arising from the second region to the second image.

9. The apparatus according to claim 1, wherein the folding optics comprises a diffraction grating.

10. The apparatus according to claim 9, wherein the diffraction grating is configured to generate a plurality of orders of diffracted radiation in response to the received radiation, and wherein the folding optics is configured to generate the first image from one of the orders of the diffracted radiation and the second image from another of the orders of the diffracted radiation.

11. The apparatus according to claim 1, wherein the folding optics comprises at least one periscope.

12. The apparatus according to claim 11, wherein the at least one periscope comprises a first periscope which receives the radiation arising from the first region and which is configured to generate the first image and a second periscope which receives the radiation arising from the second region and which is configured to generate the second image.

13. The apparatus according to claim 12, wherein the first periscope defines a first periscope plane and the second periscope defines a second periscope plane, and wherein the first periscope plane and the second periscope plane are non-perpendicular.

14. The apparatus according to claim 1, further comprising an image intensifier (IIT), located before the folding optics, and wherein the radiation comprises a first intensified image of the first region and a second intensified image of the second region, the first intensified image and the second intensified image being generated by the IIT.

15. The apparatus according to claim 1, further comprising an image intensifier (IIT) located between the detector and the folding optics, and wherein the first image comprises a first intensified image and the second image comprises a second intensified image, the first intensified image and the second intensified image being generated by the IIT.

16. The apparatus according to claim 1, wherein the folding optics comprises a beamsplitter adapted to form the first image as a reflected image from the beamsplitter and to form the second image as a transmitted image through the beamsplitter.

17. A method for inspecting a surface of a sample, comprising:
receiving at folding optics radiation arising from a first region of the surface and radiation arising from a second region of the surface, the first and second regions having a first spatial relationship with respect to each other;
forming from the radiation in the folding optics a first image of the first region and a second image of the second region on a detector, wherein each of the first and second images on the detector is a linear transformation of the corresponding first and second regions of the surface;
arranging, using the folding optics, the first and second images according to a second spatial relationship, different from a linear transformation of the first spatial relationship, with respect to each other; and
arranging, using the folding optics, the first and second images according to the second spatial relationship so as to more completely fill the detector compared to arranging the first and second images according to the linear transformation of the first spatial relationship.

18. The method according to claim 17, wherein the folding optics comprises at least one fiber optic bundle.

19. The method according to claim 18, wherein the at least one fiber optic bundle comprises a first fiber optic bundle which receives the radiation arising from the first region and which is configured to transfer the radiation arising from the first region to the first image and a second fiber optic bundle which receives the radiation arising from the second region and which is configured to transfer the radiation arising from the second region to the second image.

20. The method according to claim 17, wherein the folding optics comprises a diffraction grating.

21. The method according to claim 20, wherein the diffraction grating is configured to generate a plurality of orders of diffracted radiation in response to the received radiation, and wherein the folding optics is configured to generate the first image from one of the orders of the diffracted radiation and the second image from another of the orders of the diffracted radiation.

22. The method according to claim 17, wherein the folding optics comprises at least one periscope.

23. The method according to claim 22, wherein the at least one periscope comprises a first periscope which receives the radiation arising from the first region and which is configured to generate the first image and a second periscope which receives the radiation arising from the second region and which is configured to generate the second image.

* * * * *